US012551668B2

(12) United States Patent
Murphy

(10) Patent No.: US 12,551,668 B2
(45) Date of Patent: Feb. 17, 2026

(54) ANGIOPLASTY BALLOON CATHETER COMPRISING A BIAXIAL-COAXIAL TRANSITION

(71) Applicant: Timothy Patrick Murphy, Providence, RI (US)

(72) Inventor: Timothy Patrick Murphy, Providence, RI (US)

( * ) Notice: Subject to any disclaimer, the term of this patent is extended or adjusted under 35 U.S.C. 154(b) by 439 days.

(21) Appl. No.: 18/106,262

(22) Filed: Feb. 6, 2023

(65) Prior Publication Data

US 2023/0191092 A1 Jun. 22, 2023

Related U.S. Application Data

(63) Continuation-in-part of application No. 16/866,907, filed on May 5, 2020, now abandoned.

(60) Provisional application No. 63/389,906, filed on Jul. 17, 2022.

(51) Int. Cl.
*A61M 25/10* (2013.01)

(52) U.S. Cl.
CPC .... *A61M 25/104* (2013.01); *A61M 25/10181* (2013.11); *A61M 2025/1056* (2013.01)

(58) Field of Classification Search
CPC .......... A61M 25/0015; A61M 25/0023; A61M 25/0026; A61M 25/0028; A61M 25/0029; A61M 25/0052; A61M 25/007; A61M 25/0169; A61M 25/0172; A61M 25/09041; A61M 25/10; A61M 25/10181; A61M 25/104; A61M 2025/0031; A61M 2025/0034; A61M 2025/018; A61M 2025/0183; A61M 2025/0188; A61M 2025/1043; A61M 2025/1056; A61M 2025/1063; A61M 2025/1081
See application file for complete search history.

(56) References Cited

U.S. PATENT DOCUMENTS

| | | | |
|---|---|---|---|
| 4,195,637 | A | 4/1980 | Gruntzig |
| 4,323,071 | A | 4/1982 | Simpson |
| 4,601,713 | A | 7/1986 | Fuqua |
| 4,641,654 | A | 2/1987 | Samson |
| 4,748,982 | A | 6/1988 | Horzewski |
| 4,762,129 | A | 8/1988 | Bonzel |
| 4,771,777 | A | 9/1988 | Horzewski |
| 4,790,315 | A | 12/1988 | Mueller |
| 4,819,751 | A | 4/1989 | Shimada |
| 4,824,435 | A | 4/1989 | Giesy |
| 4,842,590 | A | 6/1989 | Tanabe |
| 4,850,969 | A | 7/1989 | Jackson |
| 4,909,252 | A | 3/1990 | Goldberger |
| 4,909,781 | A | 3/1990 | Husted |
| 4,944,745 | A | 7/1990 | Sogard |
| 4,983,167 | A | 1/1991 | Sahota |

(Continued)

*Primary Examiner* — Robert A Lynch

(57) ABSTRACT

The disclosed invention is in the field of medical devices, namely angioplasty balloon catheters. The embodiments provide an angioplasty balloon catheter that has favorable features of both biaxial and coaxial lumen configurations, such as pushability, torque, and trackability, enabled by a transition between a biaxial catheter segment and a coaxial catheter segment. In an exemplary embodiment a biaxial-coaxial lumen configuration facilitates injection of fluids through the catheter and out of the catheter proximal to its distal tip end with a guidewire in place in the catheter.

12 Claims, 5 Drawing Sheets

(56) References Cited

U.S. PATENT DOCUMENTS

| | | | | |
|---|---|---|---|---|
| 4,988,356 | A | | 1/1991 | Crittenden |
| 4,994,033 | A | | 2/1991 | Shockey |
| 5,040,548 | A | | 8/1991 | Yock |
| 5,046,497 | A | | 9/1991 | Millar |
| 5,046,503 | A | | 9/1991 | Schneiderman |
| 5,049,131 | A | | 9/1991 | Deuss |
| 5,061,273 | A | | 10/1991 | Yock |
| 5,078,685 | A | | 1/1992 | Colliver |
| 5,087,247 | A | | 2/1992 | Horn |
| 5,102,403 | A | | 4/1992 | Alt |
| 5,108,370 | A | | 4/1992 | Walinsky |
| 5,116,318 | A | | 5/1992 | Hillstead |
| 5,135,535 | A | | 8/1992 | Kramer |
| 5,147,377 | A | | 9/1992 | Sahota |
| 5,154,725 | A | | 10/1992 | Leopold |
| 5,156,594 | A | | 10/1992 | Keith |
| 5,158,540 | A | | 10/1992 | Wijay |
| 5,171,222 | A | | 12/1992 | Euteneuer |
| 5,180,367 | A | | 1/1993 | Kontos |
| 5,205,822 | A | | 4/1993 | Johnson |
| 5,232,445 | A | | 8/1993 | Bonzel |
| 5,267,958 | A | | 12/1993 | Buchbinder |
| 5,284,473 | A | | 2/1994 | Calabria |
| 5,295,959 | A | | 3/1994 | Gurbel |
| 5,295,995 | A | | 3/1994 | Kleiman |
| 5,308,356 | A | | 5/1994 | Blackshear |
| 5,318,535 | A | | 6/1994 | Miraki |
| 5,324,269 | A | | 6/1994 | Miraki |
| 5,328,469 | A | | 7/1994 | Coletti |
| 5,336,184 | A | | 8/1994 | Teirstein |
| 5,342,297 | A | | 8/1994 | Jang |
| 5,346,505 | A | | 9/1994 | Leopold |
| 5,370,617 | A | | 12/1994 | Sahota |
| 5,378,237 | A | | 1/1995 | Boussignac |
| 5,383,853 | A | | 1/1995 | Jung |
| 5,383,856 | A | | 1/1995 | Bersin |
| 5,383,890 | A | | 1/1995 | Miraki |
| 5,395,333 | A | | 3/1995 | Brill |
| 5,395,353 | A | | 3/1995 | Scribner |
| 5,403,274 | A | | 4/1995 | Cannon |
| 5,409,458 | A | | 4/1995 | Khairkhahan |
| 5,411,478 | A | | 5/1995 | Stillabower |
| 5,425,709 | A | | 6/1995 | Gambale |
| 5,425,714 | A | | 6/1995 | Johnson |
| 5,433,706 | A | | 7/1995 | Abiuso |
| 5,470,314 | A | | 11/1995 | Walinsky |
| 5,472,425 | A | | 12/1995 | Teirstein |
| 5,484,411 | A | | 1/1996 | Inderbitzen |
| 5,484,412 | A | | 1/1996 | Pierpont |
| 5,489,271 | A | | 2/1996 | Anderson |
| 5,538,510 | A | | 7/1996 | Fontirroche |
| 5,554,118 | A | * | 9/1996 | Jang .................. A61M 25/0023 604/523 |
| 5,769,814 | A | * | 6/1998 | Wijay ................. A61M 25/104 604/103.1 |
| 5,879,324 | A | * | 3/1999 | von Hoffmann ... A61M 25/104 604/523 |
| 6,007,517 | A | | 12/1999 | Anderson |
| 6,322,577 | B1 | | 11/2001 | McInnes |
| 6,402,720 | B1 | | 6/2002 | Miller |
| 6,702,781 | B1 | | 3/2004 | Reifart |
| 7,873,404 | B1 | | 1/2011 | Patton |
| 8,532,749 | B1 | | 9/2013 | Patton |
| 10,149,962 | B2 | | 12/2018 | Franklin |
| 2004/0267239 | A1 | * | 12/2004 | Jang ..................... A61B 8/4461 604/509 |
| 2016/0331944 | A1 | * | 11/2016 | Tal ......................... A61B 6/504 |

* cited by examiner

ANGIOPLASTY BALLOON CATHETER COMPRISING A BIAXIAL-COAXIAL TRANSITION

CROSS-REFERENCE TO RELATED APPLICATIONS

This application claims priority under 35 U.S.C. § 119 and 35 U.S.C. § 120 of provisional patent application No. 63/389,906, EFS ID 46206444, confirmation number 4427, filed 17 Jul. 2022, entitled "Angioplasty Balloon Catheter Comprising a Biaxial-Coaxial Transition", by inventor Timothy Murphy, the entirety of which is incorporated herein by reference. This application is a Continuation-In-Part under 37 CFR 1.53(b) of patent application Ser. No. 16/866,907, EFS ID 39354524, filed 5 May 2020, and claims the benefit of the prior application under 35 U.S.C. § 120.

FIELD OF THE INVENTION

The present invention relates to medical devices and medical vascular interventional methods. More particularly, the present invention is directed to medical devices used for angioplasty of intravascular stenoses, and methods of use thereof.

BACKGROUND

U.S. Patents

| Patent Number | Issue Date | Patentee |
|---|---|---|
| U.S. Pat. No. 10,149,962 | Dec. 11, 2018 | Franklin |
| U.S. Pat. No. 8,532,749 | Sep. 10, 2013 | Patton |
| U.S. Pat. No. 7,873,404 | Jan. 18, 2011 | Patton |
| U.S. Pat. No. 6,702,781 | Mar. 9, 2004 | Reifart |
| U.S. Pat. No. 6,402,720 | Jun. 11, 2002 | Miller |
| U.S. Pat. No. 6,322,577 | Nov. 27, 2001 | McInnes |
| U.S. Pat. No. 6,007,517 | Dec. 28, 1999 | Anderson |
| U.S. Pat. No. 5,538,510 | Jul. 23, 1996 | Fontirroche |
| U.S. Pat. No. 5,489,271 | Feb. 6, 1996 | Anderson |
| U.S. Pat. No. 5,484,412 | Jan. 16, 1996 | Pierpont |
| U.S. Pat. No. 5,484,411 | Jan. 16, 1996 | Inderbitzen et al. |
| U.S. Pat. No. 5,472,425 | Apr. 22, 1994 | Teirstein |
| U.S. Pat. No. 5,472,425 | Dec. 5, 1995 | Teirstein |
| U.S. Pat. No. 5,470,314 | Nov. 28, 1995 | Walinsky |
| U.S. Pat. No. 5,433,706 | Jul. 18, 1995 | Abiuso |
| U.S. Pat. No. 5,425,714 | Jun. 20, 1995 | Johnson et al. |
| U.S. Pat. No. 5,425,709 | Jun. 20, 1995 | Gambale |
| U.S. Pat. No. 5,411,478 | May 2, 1995 | Stillabower |
| U.S. Pat. No. 5,409,458 | Apr. 25, 1995 | Khairkhahan et al. |
| U.S. Pat. No. 5,403,274 | Apr. 4, 1995 | Cannon |
| U.S. Pat. No. 5,395,353 | Mar. 7, 1995 | Scribner |
| U.S. Pat. No. 5,395,333 | Mar. 7, 1995 | Brill |
| U.S. Pat. No. 5,383,890 | Jan. 24, 1995 | Miraki et al. |
| U.S. Pat. No. 5,383,856 | Jan. 24, 1995 | Bersin |
| U.S. Pat. No. 5,383,853 | Jan. 24, 1995 | Jung |
| U.S. Pat. No. 5,378,237 | Jan. 3, 1995 | Boussignac et al. |
| U.S. Pat. No. 5,370,617 | Dec. 6, 1994 | Sahota |
| U.S. Pat. No. 5,346,505 | Sep. 13, 1994 | Leopold |
| U.S. Pat. No. 5,342,297 | Aug. 30, 1994 | Jang |
| U.S. Pat. No. 5,336,184 | Aug. 9, 1994 | Teirstein |
| U.S. Pat. No. 5,336,184 | Aug. 9, 1994 | Teirstein |
| U.S. Pat. No. 5,328,469 | Jul. 12, 1994 | Coletti |
| U.S. Pat. No. 5,324,269 | Jun. 28, 1994 | Miraki |
| U.S. Pat. No. 5,318,535 | Jun. 7, 1994 | Miraki |
| U.S. Pat. No. 5,308,356 | May 3, 1994 | Blackshear, Jr. et al. |
| U.S. Pat. No. 5,295,995 | Mar. 22, 1994 | Kleiman |
| U.S. Pat. No. 5,295,959 | Mar. 22, 1994 | Gurbel et al. |
| U.S. Pat. No. 5,284,473 | Feb. 8, 1994 | Calabria |
| U.S. Pat. No. 5,267,958 | Dec. 7, 1993 | Buchbinder et al. |
| U.S. Pat. No. 5,232,445 | Aug. 3, 1993 | Bonzel |

-continued

U.S. Patents

| Patent Number | Issue Date | Patentee |
|---|---|---|
| U.S. Pat. No. 5,205,822 | Apr. 27, 1993 | Johnson et al. |
| U.S. Pat. No. 5,180,367 | Jan. 19, 1993 | Kontos et al. |
| U.S. Pat. No. 5,171,222 | Dec. 15, 1992 | Euteneuer et al. |
| U.S. Pat. No. 5,158,540 | Oct. 27, 1992 | Wijay et al. |
| U.S. Pat. No. 5,156,594 | Oct. 20, 1992 | Keith |
| U.S. Pat. No. 5,156,594 | Oct. 20, 1992 | Keith |
| U.S. Pat. No. 5,154,725 | Oct. 13, 1992 | Leopold |
| U.S. Pat. No. 5,147,377 | Sep. 15, 1992 | Sahota |
| U.S. Pat. No. 5,135,535 | Aug. 4, 1992 | Kramer |
| U.S. Pat. No. 5,116,318 | May 26, 1992 | Hillstead |
| U.S. Pat. No. 5,108,370 | Apr. 28, 1992 | Walinsky |
| U.S. Pat. No. 5,102,403 | Apr. 7, 1992 | Alt |
| U.S. Pat. No. 5,087,247 | Feb. 11, 1992 | Horn |
| U.S. Pat. No. 5,078,685 | Jan. 7, 1992 | Colliver |
| U.S. Pat. No. 5,061,273 | Oct. 29, 1991 | Yock |
| U.S. Pat. No. 5,061,273 | Oct. 29, 1991 | Yock |
| U.S. Pat. No. 5,049,131 | Sep. 17, 1991 | Deuss |
| U.S. Pat. No. 5,046,503 | Sep. 10, 1991 | Schneiderman |
| U.S. Pat. No. 5,046,497 | Sep. 10, 1991 | Millar |
| U.S. Pat. No. 5,040,548 | Aug. 20, 1991 | Yock |
| U.S. Pat. No. 5,040,548 | Aug. 20, 1991 | Yock |
| U.S. Pat. No. 4,994,033 | Feb. 19, 1991 | Shockey et al. |
| U.S. Pat. No. 4,988,356 | Jan. 29, 1991 | Crittenden |
| U.S. Pat. No. 4,988,356 | Jan. 29, 1991 | Crittenden et al. |
| U.S. Pat. No. 4,983,167 | Jan. 8, 1991 | Sahota |
| U.S. Pat. No. 4,944,745 | Jul. 31, 1990 | Sogard et al. |
| U.S. Pat. No. 4,909,781 | Mar. 20, 1990 | Husted |
| U.S. Pat. No. 4,909,252 | Mar. 20, 1990 | Goldberger |
| U.S. Pat. No. 4,850,969 | Jul. 25, 1989 | Jackson |
| U.S. Pat. No. 4,842,590 | Jun. 27, 1989 | Tanabe |
| U.S. Pat. No. 4,824,435 | Apr. 25, 1989 | Giesy |
| U.S. Pat. No. 4,819,751 | Apr. 11, 1989 | Shimada et al. |
| U.S. Pat. No. 4,790,315 | Dec. 13, 1988 | Mueller, Jr. et al. |
| U.S. Pat. No. 4,771,777 | Sep. 20, 1988 | Horzewski |
| U.S. Pat. No. 4,762,129 | Aug. 9, 1988 | Bonzel |
| U.S. Pat. No. 4,762,129 | Aug. 9, 1988 | Bonzel |
| U.S. Pat. No. 4,748,982 | Jun. 7, 1988 | Horzewski |
| U.S. Pat. No. 4,641,654 | Feb. 10, 1987 | Samson |
| U.S. Pat. No. 4,601,713 | Jul. 22, 1986 | Fuqua |
| U.S. Pat. No. 4,581,017 | Apr. 8, 1986 | Sahota |
| U.S. Pat. No. 4,581,017 | April, 1986 | Sahota |
| U.S. Pat. No. 4,323,071 | Apr. 6, 1982 | Simpson |
| U.S. Pat. No. 4,195,637 | Apr. 1, 1980 | Gruntzig |
| U.S. Pat. No. 3,382,872 | May 1, 1968 | Rubin |

U.S. Patent Application

Patent Appl. No. US 2005/0027249 Publication Date 2/3/2005 Reifart

Foreign Patent Application

German patent application P 39 34 695.1 Rupprecht

PUBLICATIONS

Nordenstrom, B. Balloon catheters for percutaneous insertion into the vascular system. Acta Radiol 1962; 57:411-416.

Nordenstrom, B. New instruments for catheterization and angiocardiography. Radiology 1965; 85:256-259.

This description of art is not intended to constitute an admission that any patent, publication, or other information referred to is "prior art" with respect to the invention unless specifically designated as such. In addition, this section should not be construed to mean that a search has been made or that no other pertinent information as defined in 37 C.F.R. § 1.56(a) exists.

An angioplasty balloon catheter comprises a tubular element with an expansile balloon generally disposed toward a distal end. Generally, angioplasty balloon catheters comprise at least two lumens, which are tubular channels surrounded by catheter walls, said tubular channels commonly being generally round in cross-section but also comprising semi-circles, crescents, or other shapes in cross-section, each lumen further comprising a longitudinal axis generally disposed longitudinally through said lumen through a point generally in the center of a cross-section of a substantially circular lumen, or through a point in a cross-section of a noncircular lumen generally located substantially equidistant on average from every point located on a circumference of said noncircular lumen cross-section as possible such that the sum of all radii connecting said center of said longitudinal axis is the smallest possible value, said at least two lumens comprising at least a first lumen for passage of a guidewire or injection of fluids therethrough, and at least a second lumen as a means for inflation of said expansile member.

Angioplasty balloon catheters typically comprise at least two lumens that can be disposed in relation to each other in either a side-by-side arrangement ("biaxial"), or alternatively a concentric arrangement, said concentric arrangement being substantially a tube-within-a-tube ("coaxial"). Biaxial angioplasty balloon catheters typically have larger outer diameters (O.D.'s) than coaxial angioplasty balloon catheters, and can be extruded together, reducing manufacturing costs compare to coaxial angioplasty balloon catheters, which are typically extruded separately and must be assembled. Furthermore, larger catheters have more "pushability", or the ability of the catheter to provide more forward force at a distance when advanced by an operator, and "torqueability" or responsiveness at a tip end from a rotational movement by an operator working at a hub end. Coaxial angioplasty balloon catheters offer efficiency because the cross-sectional area of a second lumen for balloon inflation is an outer lumen, and can be larger for a given cross-sectional area compared to a biaxial angioplasty balloon catheter, providing better balloon inflation and deflation performance compared to biaxial angioplasty balloon catheters of the same O.D. Smaller catheters generally have less pushability and torqueability than larger catheters, but have better "trackability", or the ability to move forward easily in distal, small blood vessels when advanced by an operator by manipulation of a proximal catheter end.

Angioplasty procedures are usually performed using percutaneous access to a blood vessel by the Seldinger technique. The Seldinger technique involves placement of a needle through the skin into a blood vessel, passage of a guidewire through a lumen of the needle into the blood vessel, and removal of the needle and replacement with a plastic diagnostic catheter. Once Seldinger access of a catheter into a blood vessel is achieved, the guidewire and catheter combination are used by an operator to selectively catheterize a blood vessel with a blockage to be treated, arteriograms are obtained, and then an angioplasty balloon catheter is substituted for the diagnostic catheter and positioned so that an expansile balloon disposed toward a tip end of said angioplasty balloon catheter is generally positioned centrally within said blockage. Said angioplasty balloon is then expanded typically by injection of fluids into a lumen in communication with an interior of said angioplasty balloon, thereby relieving the said blockage. Said expansile balloon is then deflated by aspiration of said injected fluids, and then the catheter is removed entirely from the body.

Angioplasty balloon catheters have been used to dilate blockages in blood vessels for over 45 years. The original angioplasty balloon catheter as used by Gruentzig in 1977 was a fixed-wire platform. Subsequently, Simpson and Robert developed a movable guidewire balloon platform, or "over-the-wire" ("OTW"), U.S. Pat. No. 4,323,071. The OTW configuration includes a lumen used to inflate an angioplasty balloon and usually a second lumen used for passage of a guidewire therethrough. In the OTW configuration, the guidewire exit port is usually at the distal tip of the catheter, and the guidewire entry port is at the hub or proximal end of the catheter.

In 1984 Bonzel introduced the concept of the "rapid exchange" ("RX"), or monorail, configuration, U.S. Pat. No. 4,762,129. With the RX configuration, the guidewire exit port is at the distal tip of the catheter, but the guidewire entry port is substantially distal to the hub or proximal end of the catheter and proximal to an angioplasty balloon.

Although angioplasty balloon catheters have existed for over 45 years and millions of angioplasty procedures are done annually in the U.S., there is a long-felt unmet need of reducing catheter exchanges between diagnostic catheters and therapeutic angioplasty balloon catheters during an angioplasty procedure. Typically, angioplasty balloon catheters are used only for therapeutic purpose of expanding a blockage in a blood vessel. Although angioplasty balloon catheters typically have a guidewire lumen that can be used for injection of fluids, angioplasty balloon catheters typically are not adapted to perform diagnostic functions such as diagnostic angiography, and using an angioplasty balloon catheter for diagnostic angiography by injection of radiopaque fluids through a guidewire lumen would require the guidewire to be absent during the injection of radiopaque fluids, thereby jeopardizing access into a more distal artery that is ensured when a guidewire is in place. Therefore, diagnostic angiography is typically performed with a diagnostic catheter, then the diagnostic catheter removed and replaced with an angioplasty balloon catheter for performance of an angioplasty, then said angioplasty balloon catheter removed and replaced with a diagnostic catheter again to perform a completion angiography.

SUMMARY

In an exemplary embodiment of the invention, an angioplasty balloon catheter with a biaxial-coaxial transition combines a biaxial proximal catheter shaft with a coaxial distal catheter shaft, thereby achieving the optimal pushability and torqueability of a larger, biaxial proximal catheter shaft with the trackability of a smaller, coaxial distal catheter shaft, by hybridizing a biaxial proximal catheter shaft with a coaxial distal catheter shaft by bonding them together, typically using heat.

Furthermore, it may be desirable in some applications that angioplasty balloon catheters have the capability of accommodating injection of fluids, such as for example radiopaque contrast, proximal or distal to an expansile balloon while a guidewire remains in place throughout a lumen of said angioplasty balloon catheter, for example as described in *Patton* (U.S. Pat. No. 7,873,404B1, U.S. Pat. No. 8,532,749B1). One design of an angioplasty balloon catheter that comprises such an injectability feature would be for each function to have a dedicated lumen, thereby requiring at least three lumens, including at least a guidewire lumen, at least a lumen for inflation and deflation of an expansile balloon, and at least a lumen for injection of fluids such as for example radiopaque contrast. However, miniaturization of device O.D. is always desirable, and a three-lumen angioplasty balloon catheter is disadvantageous in terms of O.D., because each lumen requires not only enough cross-sectional area to perform its function, but also for its outer walls. To reduce overall O.D., it is desirable that multiple functions are shared within a single lumen, for example, a guidewire lumen configured also to accommodate injection of fluids. Having at least one multifunction lumen allows all three functions, injectability, balloon inflation-deflation, and guidewire traversal, to be accommodated with fewer than three lumens, i.e., with one or two lumens.

One exemplary way to design a single lumen for multiple functions would be to over-size a lumen such that it is of sufficiently larger cross-sectional area than required for its typical guidewire, so that sufficient flow rates can be achieved when fluids are injected into the same lumen even with a guidewire in place therethrough. This design would require a hub adapter that conforms to a guidewire in a substantially fluid-tight manner forming a choke around said guidewire, but also incorporating an injection port distal to said fluid-tight choke, such as a Touhy-Borst adapter or a hemostasis valve adapter with an injection side port distal to a valve or alternatively a compressible O-ring or disk that deforms to adapt to a fluid-tight configuration around said guidewire when a component of a hub is tightened or otherwise manipulated by an operator. Once injected, fluids flow around said guide and also require an exit port, which may be accommodated by a distal endhole that is sufficiently larger than a typical guidewire to allow contrast to exit from a distal tip end of the angioplasty balloon catheter. Or, as an alternative exemplary embodiment, an injection exit port may comprise at least one sidehole through a sidewall of a catheter shaft, either proximal or distal to an expansile balloon but proximal to a catheter distal endhole. Such a design could be accomplished with a catheter having a biaxial or coaxial lumen configuration. In that exemplary embodiment, said injection exit port could be proximal to a guidewire exit port for a catheter used in a "rapid exchange" configuration, or distal to said guidewire exit port.

However, oversizing a single lumen for multiple functions throughout a length of an angioplasty balloon catheter results in an O.D. that may be larger than desired for performing an angioplasty of a small blood vessel, such as for example a blood vessel in a lower leg or foot. For small vessel angioplasty, coaxial angioplasty balloon catheter configurations are preferred, since they can be made with smaller O.D.'s and yet still have similar balloon inflation-deflation performance as biaxial angioplasty configurations with larger O.D's. For a small vessel angioplasty, when fluid injection is desired, a preferred embodiment of the invention is an angioplasty balloon catheter that combines a biaxial segment proximally that incorporates at least a lumen for inflation-deflation of an expansile balloon and at least a multifunction lumen comprising guidewire passage and injectability, with a smaller distal coaxial segment that only accommodates guidewire passage and inflation-deflation of an expansile balloon. In such an exemplary embodiment, fluid injectability would only be accommodated through the proximal biaxial segment, and therefore at least an injection exit port would need to be disposed along said biaxial proximal catheter segment, or within a transition between a proximal biaxial segment and a distal coaxial segment.

Although balloon angioplasty procedures have been performed on human patients for over 45 years, and there are more than a million balloon angioplasty procedures performed each year by highly skilled practitioners, and those practitioners desire to reduce catheter exchanges and thereby reduce overall procedure time to benefit their patients, angioplasty balloon catheters typically have not incorporated an injectability feature with a guidewire in place therethrough until recently. Injectability of an angioplasty balloon catheter can be achieved using a biaxial lumen throughout said angioplasty balloon catheter, by oversizing a guidewire lumen proximal to an exit sidehole to accommodate radiopaque or other fluid injection around said guidwire in a solution that could be considered obvious, such as that provided by the "Chameleon" angioplasty balloon catheter (Medtronic, Minneapolis, Minnesota). However, providing injectability in an angioplasty balloon catheter using a biaxial-coaxial catheter as described herein is not obvious because the lumens don't naturally align. That is, to achieve injectability with a biaxial-coaxial catheter there must be a transition where the lumens are brought into alignment, and therefore it is not obvious that combining a larger proximal biaxial catheter segment with a smaller distal coaxial segment would provide a solution. Accommodating that transition by reducing the size of a first lumen for injection of fluids or passage of a guidewire therethrough and incorporating said first lumen within a second lumen for inflation-deflation of an expansile balloon in a coaxial configuration is a nonobvious inventive step.

In accordance with one form of the invention, an angioplasty balloon catheter comprising a biaxial-coaxial transition comprises a hub end and a tip end, between which there is a tubular shaft, upon said tubular shaft there is an expansile balloon generally disposed toward said tip end of said tubular shaft, and a hub adapter at said hub end comprising two injection ports, said two injection ports being in continuity with at least two lumens within said shaft, said at least two lumens comprising at least a first lumen for passage of a guidewire or injection of fluids therethrough, and at least a second lumen as a means for inflation of said expansile balloon.

Furthermore, in accordance with one exemplary form of the invention, an angioplasty balloon catheter comprising a biaxial-coaxial transition further comprises at least a proximal shaft further comprising at least two lumens that are biaxially oriented in relation to each other, meaning that their lumen cross-sectional areas do not overlap but rather are side by side, and at least a distal shaft comprising at least two lumens that are coaxially oriented in relation to each other, meaning that a cross-sectional area of an inner lumen is completely circumscribed within a cross-section area of an outer lumen cross sectional area as a "tube within a tube".

In accordance with one form of the invention, there is a transition in said shaft between said proximal shaft and said distal shaft, said transition comprising an exchange wherein said at least two lumens transform said orientation in relation to each other from biaxial to coaxial.

In some embodiments of the invention, said transition comprises a taper between a proximal biaxial segment and a distal coaxial segment, said transition having a first larger O.D. proximally and a second smaller O.D. distally. In one embodiment of the invention, said proximal biaxial segment has an O.D. of substantially between 3 and 5 French, or between 4 and 5 French, or between 4.5 and 5 French, and said distal coaxial segment has an O.D. of substantially between 2 and 3 French, or between 2.5 and 3 French. In one embodiment of the invention, said transition comprises a length of between 1 mm and 75 cm, or between 1 mm and 30 mm. Those familiar with the art will appreciate that other embodiments of the invention will comprise shaft diameters in the typical range known in the art, for example, between 2 French and 10 French.

Those familiar with the art will further appreciate that a transition from biaxial to coaxial configuration may entail thinning of a wall of a lumen, for example, said biaxial lumens may have thicker walls than said coaxial lumens, in an exemplary embodiment.

In one embodiment of the invention, said transition is disposed more distally than proximally, however, those familiar with the art will appreciate that a transition may be located anywhere between said hub end and said expansile balloon. Furthermore, those familiar with the art will readily appreciate that said at least two lumens can have many different cross-sectional shapes, for example, a biaxial configuration may comprise lumens with cross-sections that are generally circular or not circular. For example, biaxial lumens can have cross-sections that are generally ovals, semi-circles, D-shaped, or crescents, and oval, semi-circular, D-shaped, crescent or other cross-section configurations can offer functional advantages as readily known to those familiar with the art.

Those familiar with the art will appreciate that in some embodiments the transition between biaxial and coaxial lumen configurations is facilitated by a reduction in the caliber of the O.D. of the catheter shaft comprising reduction of the inner diameter (I.D.) and O.D. of said first lumen from said proximal biaxial segment as said proximal biaxial segment passes distally within a transition segment, said reduction of I.D. and O.D. of said biaxial segment facilitating envelopment of said first lumen by said second lumen in a transition to said distal coaxial segment.

In an exemplary embodiment, said reduction of a first lumen I.D. in a distal coaxial segment would be small enough to accommodate a guidewire, but not large enough to accommodate substantial injection around said guidewire. For example, said I.D. could be less than 2/1000 of an inch larger than said guidewire in said distal coaxial segment.

Those familiar with the art will appreciate that an exemplary method of manufacture of said transition segment in an angioplasty balloon catheter from said proximal biaxial configuration to said distal coaxial configuration is to form a proximal biaxial catheter segment so that said first lumen migrates toward a central location of said second lumen as it moves away from said proximal biaxial segment within said transition segment towards said distal coaxial segment, in one exemplary embodiment also comprising a reduction in its O.D., and expanding an angular circumference of said second lumen so that it wraps substantially around said first lumen. In one embodiment of said exemplary method of manufacture, said transition segment comprises a heat weld between said proximal biaxial segment and said distal coaxial segment, said heal weld being achieved with the use of mandrels to preserve lumen shapes as required, in particular a tapered mandrel would be used to preserve a configuration of said first lumen throughout a transition from said proximal biaxial segment to said distal coaxial segment such that guidewire passage is facilated.

In one exemplary embodiment of the invention, a proximal biaxial catheter segment may comprise a stiffening member, such as a core wire or hypotube, to impart stiffness to said proximal biaxial segment, to confer rigidity to the overall proximal biaxial segment and oppose a tendency in the body for a catheter to kink, bend so that it assumes a spiral course in a blood vessel such as an aorta, or fold over on itself rather than tracking and advancing in a linear manner. In an exemplary embodiment, such a stiffening member may be integral to said proximal biaxial segment, irreversibly adherent to it. In another exemplary embodiment, said stiffening member may be contained within said proximal biaxial catheter segment but reversibly attached and removable from it.

In another exemplary embodiment, a transition segment comprises a region of overlap between a guidewire in situ throughout a guidewire lumen in said distal coaxial segment and a stiffening member contained in a proximal biaxial segment, said proximal biaxial segment also comprising sufficient lumen diameter to simultaneously accommodate fluid injection therethrough while said stiffening member is in place within the same lumen. Said overlap of said guidewire and said stiffening member over at least 1 mm in length would provide continuous stiffness throughout a catheter working length, thereby reducing the likelihood of catheter kinking during use, particularly at said transition segment, which might be vulnerable to said kinking if a caliber change was present therein. Similarly, a region of overlap between a guidewire used in a distal coaxial segment in a rapid exchange configuration and a stiffener in a proximal biaxial segment could occur in a distal portion of said proximal biaxial segment, if a guidewire port for exit of said guidewire were located in said proximal biaxial segment.

In one exemplary embodiment of the invention, an angioplasty balloon catheter has a "rapid exchange" configuration. That is, the catheter has a guidewire lumen that does not extend throughout substantially all of the catheter, but rather extends from a distal catheter tip proximally and then exits a side wall of said catheter through a guidewire port located between a distal tip end and a proximal hub end, generally disposed more toward a distal end than a proximal end, generally but not necessarily between an angioplasty balloon and a middle of a catheter working length. In such an exemplary embodiment, a guidewire lumen may be between 5 cm and 100 cm in length, or in other embodiments between 5 and 10 cm, 5 and 20 cm, 5 and 50 cm, or 5 and 75 cm in length.

In another exemplary embodiment, a catheter working length is extra long to enable angioplasty procedure to be performed from virtually any access point in a vascular system, for example, angioplasty of arteries distal to a knee joint performed by a radial artery access point. In such an exemplary embodiment, a catheter working length may be between 200 and 360 cm.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Devices and related methods are disclosed that generally involve the invention comprising an angioplasty balloon catheter further comprising a biaxial-coaxial transition, the means of manufacture of the invention, and the use of the invention during an angioplasty procedure.

Figure 1:
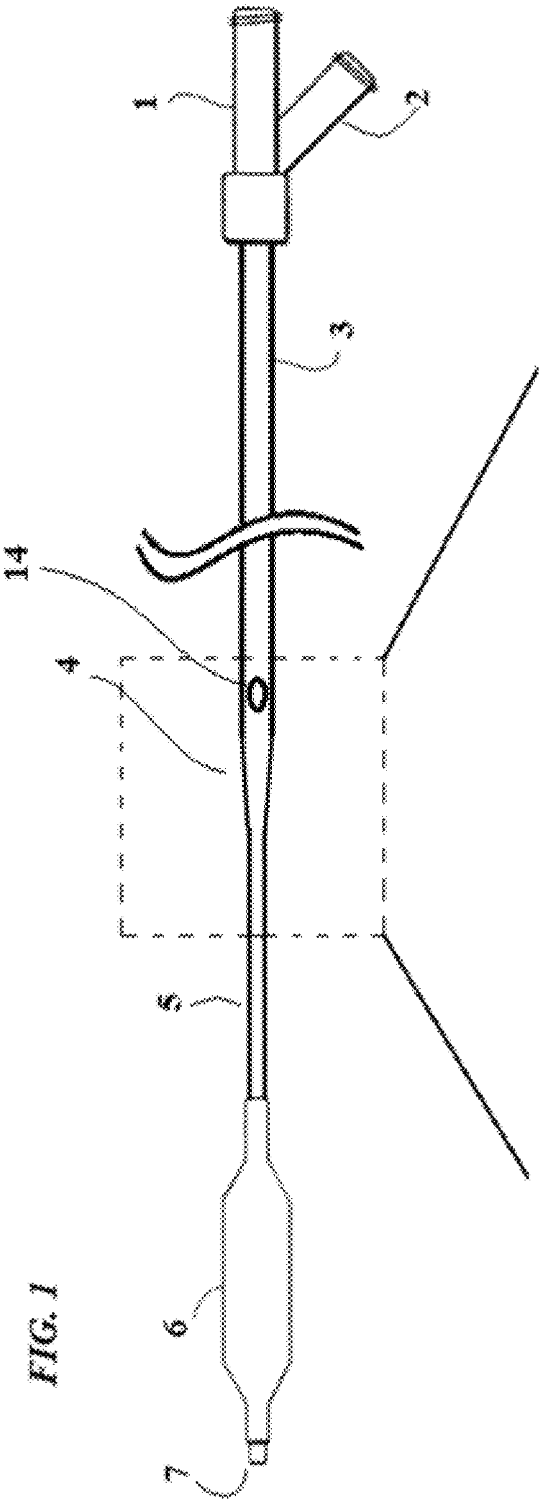
FIG. 1 depicts a preferred embodiment of the invention, in this case an angioplasty balloon catheter with a biaxial-coaxial transition segment, as seen from a lateral surface rendering view.

FIG. 1 depicts a preferred embodiment of the invention, in this case an angioplasty balloon catheter with a proximal hub end comprising a first port 1 for passage of a guidewire and injection of fluids therethrough, said proximal hub end further comprising a second port 2 as a means for injection of fluid or gas as means of inflation of an expansile balloon 6 generally disposed toward a tip end 7 of said angioplasty balloon catheter, said angioplasty balloon catheter further comprising a shaft which is a substantially tubular element generally disposed between said proximal hub end and said tip end 7, said shaft comprising at least two lumens, including at least a first lumen for passage of a guidewire and injection of fluids therethrough, and at least a second lumen for injection of fluids or gases as a means of inflation of said expansile balloon 6, said second lumen in fluid communication with an interior of said expansile balloon 6, in this preferred embodiment said shaft comprising a proximal shaft 3 which comprises two lumens oriented in a biaxial configuration in which said two lumens are substantially parallel and side-by-side, said shaft further comprising a distal shaft 5 which comprises two lumens oriented in a coaxial configuration in which one lumen is contained in and circumscribed by the other lumen, in this preferred embodiment said shaft further comprising a biaxial-coaxial transition segment 4 comprising a location for transition of the orientation of the two lumens from a proximal biaxial configuration to a distal coaxial configuration, in this preferred embodiment said biaxial-coaxial transition segment 4 being located closer to said tip end 7 than to a proximal hub end first port 1, said shaft further comprising at least one opening through a sidewall along a length of said tubular element that provides an injection exit port for egress of fluids injected into said first lumen 14. It is well-known to those in the art that said proximal shaft 3, said distal shaft 5, and said biaxial-coaxial transition segment 4 can be formed of any known material suitable for similar medical devices including such materials as polyamides, polyurethanes, polyesters, polyether ether ketones, and polyethylenes, or any combination thereof. In this preferred embodiment, said biaxial-coaxial transition segment 4 further comprises a taper, wherein said proximal shaft has a larger O.D. than said distal shaft, for example, by between 0.5 and 3 French sizes.

Figure 2:
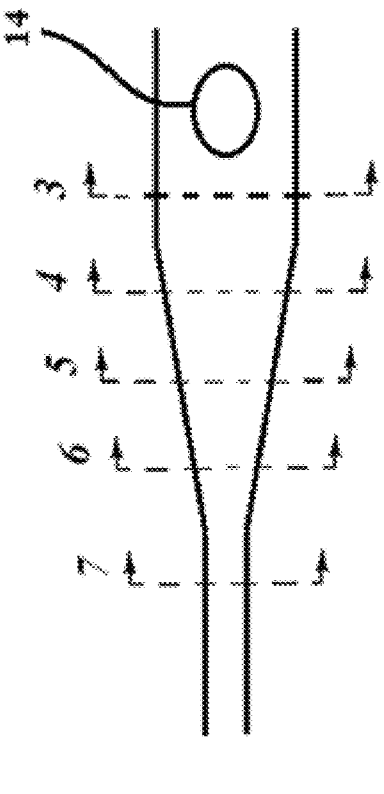
FIG. 2 is an expanded view of a biaxial-coaxial transition segment in FIG. 1. Subsequent figures are cross-section views and are labeled on this figure with the direction that the subsequent figures are viewed indicated by the direction of arrows.

FIG. 2 is an expanded view of a biaxial-coaxial transition segment 4 as shown in FIG. 1. Orientation and perspective of subsequent cross-section views are depicted using dashed lines and figure numbers for subsequent figures, arrows indicating a general perspective from which subsequent cross-section images is viewed.

Figure 3:
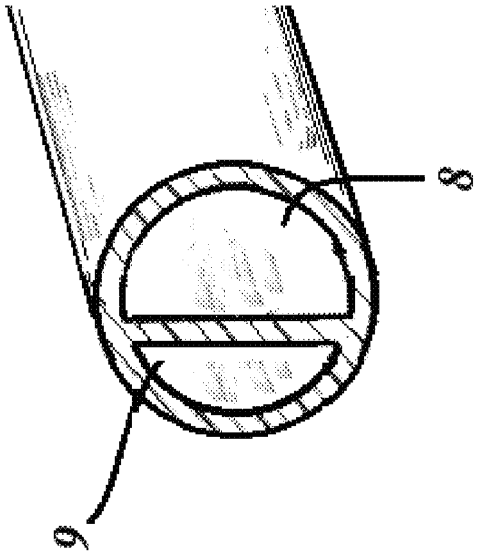
FIG. 3 is a cross-section view of a proximal biaxial segment, taken proximal to a biaxial-coaxial transition as indicated generally by the arrow labeled "3" on FIG. 2.

FIG. 3 is an exemplary view of a preferred embodiment of a proximal shaft 3, depicting a first lumen 8 for passage of a guidewire or injection of fluids therethrough, and a second lumen 9 for injection of fluids or gases as a means of inflation of said expansile balloon 6, said lumens being in a biaxial configuration.

Figure 4:
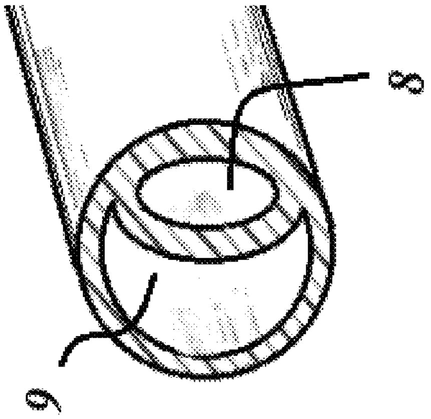
FIG. 4 is a cross-section view of FIG. 2 taken within a biaxial-coaxial transition segment disposed toward a proximal shaft, as indicated generally by the arrow labeled "4" on FIG. 2.

FIG. 4 is an exemplary view of a preferred embodiment of a biaxial-coaxial transition segment 4, depicting a first lumen 8 for passage of a guidewire or injection of fluids therethrough, and a second lumen 9 for injection of fluids or gases as a means of inflation of said expansile balloon 6, said lumens being substantially biaxial, except said second lumen 8 is transitioning from a biaxial to a coaxial configuration in this example by intrusion of said first lumen 8 into a lumen of a second lumen 9 such that a circumference of said first lumen is partially circumscribed by a circumference of said second lumen 9.

While not drawn exactly to scale, the intent of the figures of this exemplary embodiment is to convey a transition in an overall O.D. of a biaxial-coaxial transition segment 4 from larger to smaller as it passes from biaxial to coaxial segments. Moreover, while not drawn exactly to scale, the intent of the figures in this exemplary embodiment is to convey a reduction in the relative caliber of said first lumen 8 at some point in the transition from biaxial to coaxial. For example, a proximal biaxial segment 3 could have an outer diameter of 4.7 French, and a distal coaxial segment 5 outer diameter of 4.2 French, resulting in a taper of 0.5 French. Similarly, a proximal biaxial segment 3 could have an outer diameter of 4.7 French, and a distal coaxial segment 5 outer diameter of 1.7 French, resulting in a taper of 3 French. Furthermore, said first lumen diameter could also taper in some exemplary embodiments between a proximal biaxial segment and a distal coaxial segment. For example, a first lumen diameter of 0.040" in a proximal biaxial segment could taper to a diameter of 0.016" in a distal coaxial segment, thereby resulting in a reduction in cross sectional area from approximately 0.77 square millimeters to approximately 0.13 square millimeters, or a reduction in cross-sectional area of a first lumen of at least 0.5 square millimeters.

Figure 5:
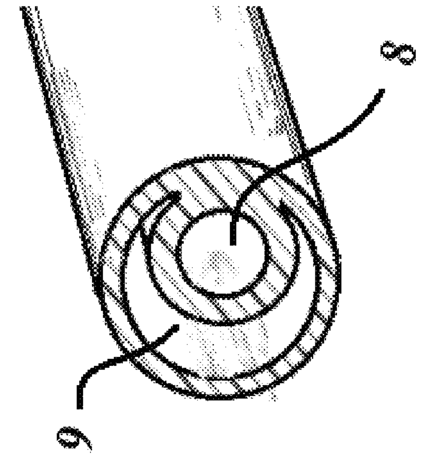
FIG. 5 is a cross-section view of FIG. 2 taken within a biaxial-coaxial transition segment, as indicated generally by the arrow labeled "5" on FIG. 2.

FIG. 5 is an exemplary view of a preferred embodiment of a biaxial-coaxial transition segment 4, depicting a first lumen 8 for passage of a guidewire or injection of fluids therethrough, and a second lumen 9 for injection of fluids or gases as a means of inflation of said expansile balloon 6, said lumens transitioning between biaxial configuration and coaxial configuration in this example by further intrusion of said first lumen 8 into a lumen of a second lumen 9 such that a greater circumference of said first lumen is partially circumscribed by a circumference of said second lumen 9 as compared to that shown in FIG. 4, having features of both biaxial and coaxial configurations because for example said second lumen 9 is circumscribed by first lumen 8 over generally 270 degrees of its circumference, but is not entirely circumscribed by first lumen 8 around 360 degrees of its circumference, and second lumen 9 over at least part of a circumference maintains physical contact with a wall of a lumen of first lumen 8.

Figure 6:
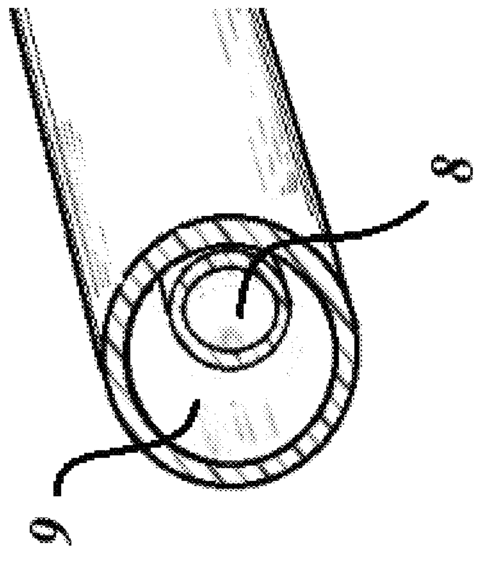
FIG. 6 is a cross-section view of FIG. 2 taken within a biaxial-coaxial transition disposed toward a distal shaft, as indicated generally by the arrow labeled "6" on FIG. 2.

FIG. 6 is an exemplary view of a preferred embodiment of the invention transition 4, depicting a first lumen 8 for passage of a guidewire or injection of fluids therethrough, and a second lumen 9 for injection of fluids or gases as a means of inflation of said expansile balloon 6, said lumens transitioning between biaxial configuration and coaxial configurations in this example by further intrusion of said first lumen 8 into a lumen of a second lumen 9 as compared to that shown in FIG. 5 such that a circumference of said first lumen is partially circumscribed by a circumference of said second lumen 9, having features of both configurations, said first lumen 8 being circumscribed by said second lumen 9 over less than 360 degrees of its circumference, second lumen 9 over at least part of a circumference maintaining physical contact with a wall of a lumen of first lumen 8, said walls of said first lumen 8 and said second lumen 9 maintaining a physical connection over at least part of their respective circumferences.

Figure 7:
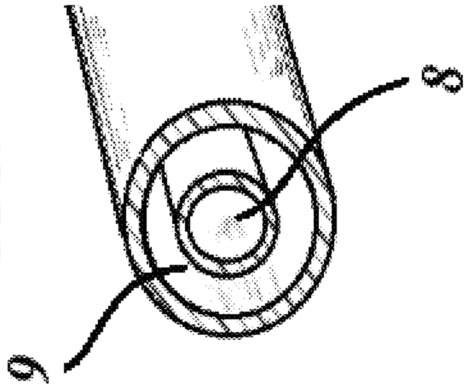
FIG. 7 is a cross-section view of a distal shaft, taken distal to a biaxial-coaxial transition segment, as indicated generally by the arrow labeled "7" on FIG. 2.

FIG. 7 is an exemplary view of a preferred embodiment of the invention distal shaft 5, depicting a first lumen 8 for passage of a guidewire or injection of fluids therethrough, and a second lumen 9 for injection of fluids or gases as a means of inflation of said expansile balloon 6, said lumens being in a coaxial configuration.

Figure 8:
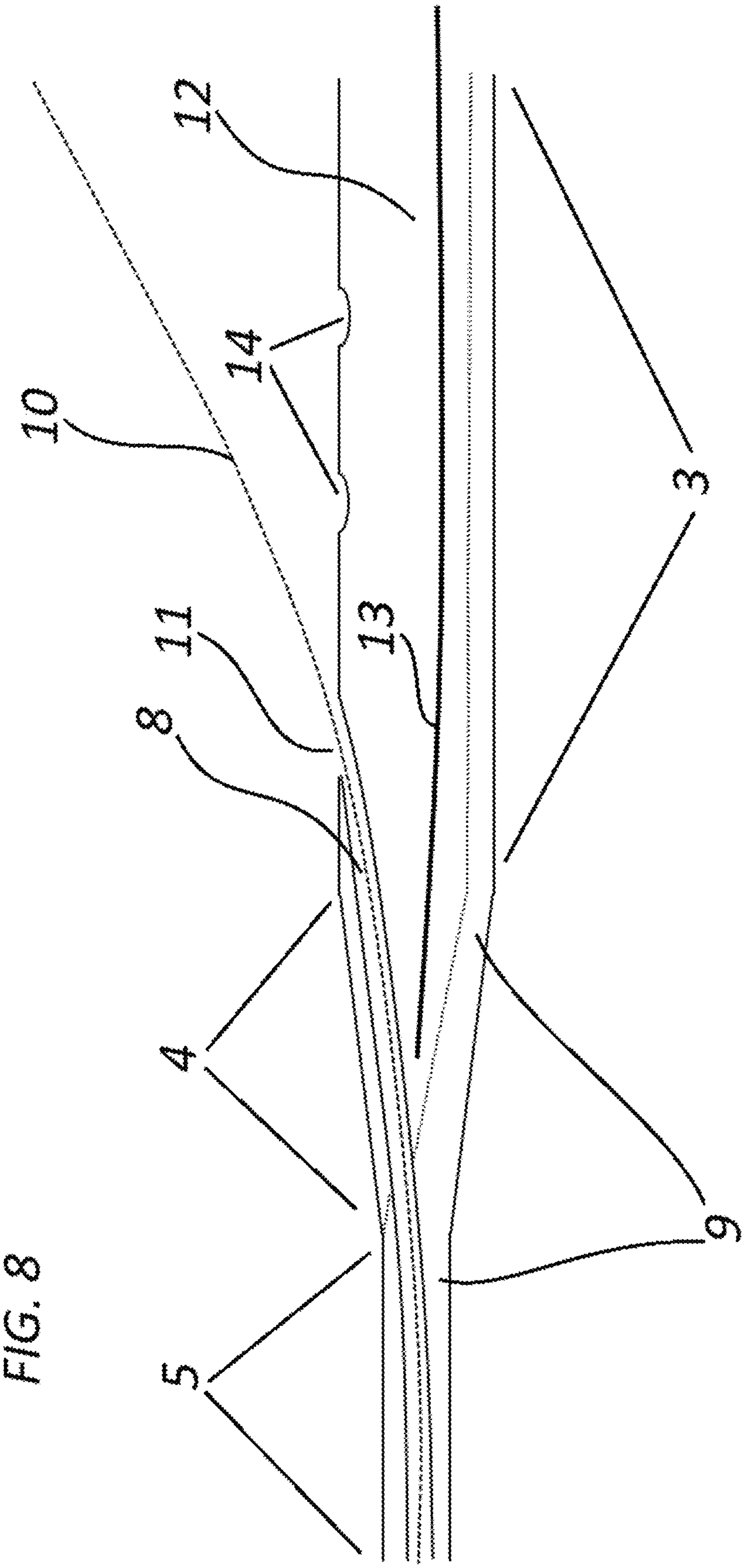
FIG. 8 is a longitudinal section of FIG. 2, depicting an exemplary embodiment of a portion of a biaxial-coaxial transition segment, also including a portion of a proximal biaxial segment and a portion of a distal coaxial segment.

FIG. 8 is a longitudinal section of FIG. 2, depicting an exemplary embodiment of a a biaxial-coaxial transition segment 4, also including a portion of a proximal biaxial segment 3 and a portion of a distal coaxial segment 5. Said distal coaxial segment 5 and said transition segment 4 comprise a guidewire lumen 8, in this illustration said guidewire lumen 8 also extends proximally into said proximal biaxial segment 3 then fuses with a proximal biaxial segment 3 sidewall and thereby in fluid communication with an exterior through a guidewire port 11. Said guidewire lumen 8 is depicted with a guidewire 10 in situ, said guidewire extending throughout a length of said distal coaxial segment 5, said biaxial-coaxial transition segment 4, and into a distal part of said proximal biaxial segment 3 before exiting through a guidewire port 11 in a side wall of said catheter. In this exemplary embodiment said catheter proximal biaxial segment 3 comprises a lumen 12 used for injection of fluids or gases as well as for locating a stiffening member 13. Said proximal biaxial segment 3 further comprises at least one injection port 14 for exit of fluids injected into said proximal biaxial segment 3 by an operator.

Figure 9:
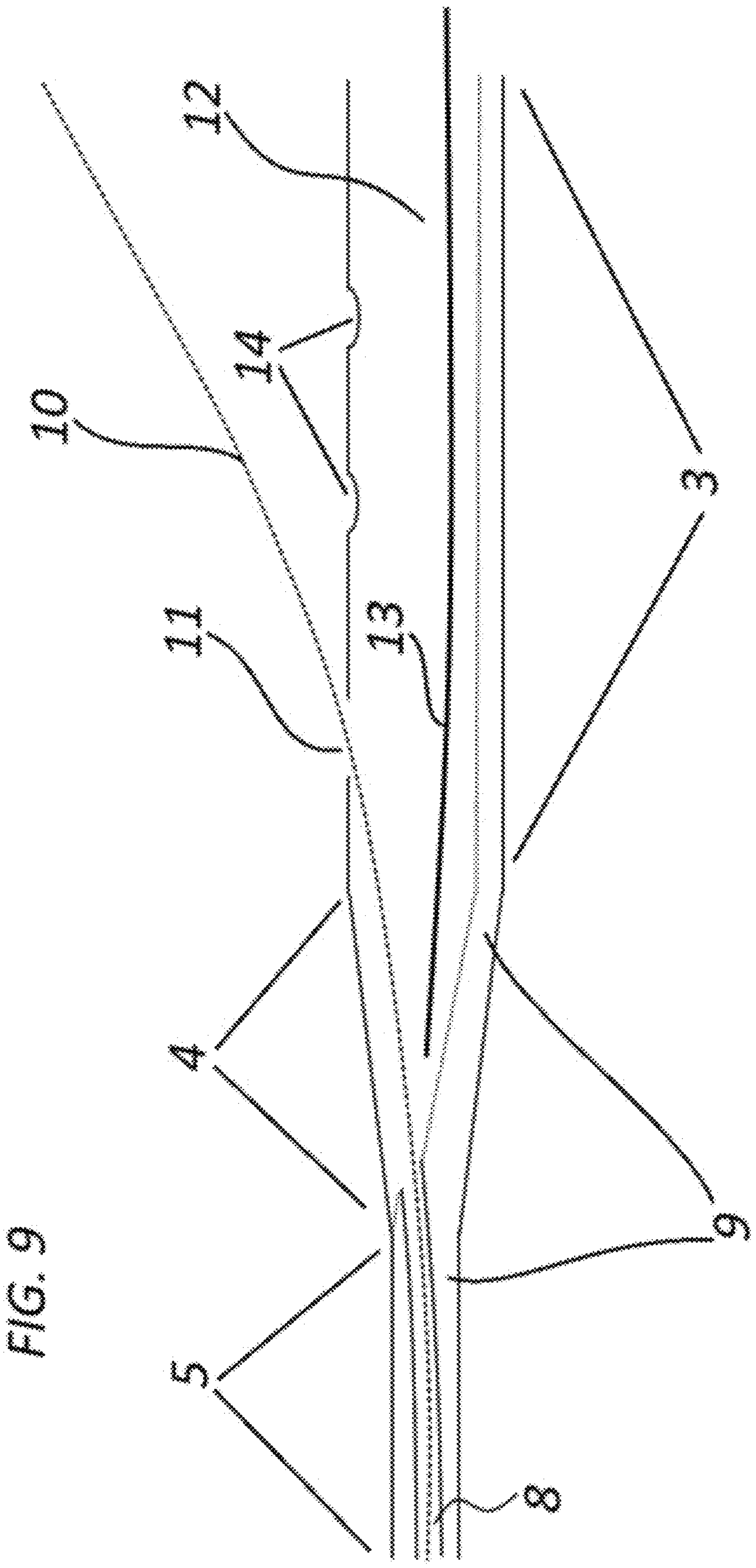
FIG. 9 is another longitudinal section of FIG. 2, depicting another exemplary embodiment of a portion of a biaxial-coaxial transition segment, also including a portion of a proximal biaxial segment and a portion of a distal coaxial segment.

FIG. 9 is a longitudinal section of FIG. 2, depicting another exemplary embodiment of a biaxial-coaxial transition segment 4, also including a portion of a proximal biaxial segment 3 and a portion of a distal coaxial segment 5. This example differs from that of FIG. 8 in that a guidewire lumen 8 does not extend proximally to fuse with a proximal biaxial segment 3 sidewall to form a guidewire port 11, but rather ends proximally within said biaxial-coaxial transition segment 4, in fluid communication with said proximal biaxial segment 3 first lumen 12. A guidewire 10 in situ in a distal coaxial segment 5 would in this embodiment pass proximally into said proximal biaxial segment 3 and then exit a guidewire port 11. Alternatively, in this embodiment, said guidewire 10 could extend proximally through a lumen 12 of said proximal biaxial segment 3 and exit the catheter through a proximal hub end first port 1, thereby comprising over-the-wire use configuration. Such a configuration could be converted between rapid exchange and over-the-wire configurations by an operator during use.

I claim:

1. An angioplasty balloon catheter comprising a tubular shaft disposed between a proximal hub end and a distal tip end, and an expansile member mounted to said tubular shaft disposed toward said distal tip end, said tubular shaft comprising at least two lumens including at least a first lumen for passage of a guidewire or injection of fluids therethrough and at least a second lumen for injection of fluids or gases to inflate and deflate said expansile member, said tubular shaft further comprising a biaxial lumen segment along less than an entire tubular shaft length and a coaxial lumen segment along less than said entire tubular shaft length, said biaxial lumen segment being disposed proximal to said coaxial lumen segment, said tubular shaft further comprising at least one opening through a sidewall along a length of said tubular shaft that provides an injection exit port for egress of fluids injected into said first lumen, said at least one opening disposed proximal to said coaxial lumen segment, said tubular shaft further comprising a transition segment between said biaxial lumen segment and said coaxial lumen segment that is disposed closer to said tip end than to said hub end, said at least one opening through a sidewall along a length of said tubular shaft located in a transition segment between said biaxial lumen segment and said coaxial lumen segment.

2. The angioplasty balloon catheter of claim 1 wherein an outer diameter of said tubular shaft biaxial lumen segment is at least 0.5 French larger than an outer diameter of said tubular shaft coaxial lumen segment.

3. The angioplasty balloon catheter of claim 1 wherein a first cross-sectional area of said first lumen in said coaxial lumen segment is smaller compared to a second cross-sectional area of said first lumen in said biaxial lumen segment by at least 0.5 square millimeters.

4. The angioplasty balloon catheter of claim 1 wherein said transition segment comprises an intrusion of said first lumen into said second lumen such that between said biaxial lumen segment and said coaxial lumen segment a circumference of said first lumen becomes progressively more circumscribed by a circumference of said second lumen until it is completely circumscribed by it around 360 degrees of its circumference.

5. The angioplasty balloon catheter of claim 1 wherein a coaxial segment outer sidewall is imperforate proximal to a distal end hole.

6. The angioplasty balloon catheter of claim 1 wherein said at least one opening through a sidewall along a length of said tubular shaft that provides an injection exit port for egress of fluids injected into said first lumen is located in said biaxial lumen segment.

7. The angioplasty balloon catheter of claim 1 wherein said first lumen for passage of a guidewire or injection of fluids therethrough is oversized to said guidewire thereby enabling injection of fluids therethrough while a guidewire resides within said first lumen in its entirety.

8. An angioplasty balloon catheter comprising a tubular shaft disposed between a proximal hub end and a distal tip end, and an expansile member mounted to said tubular shaft disposed toward said distal tip end, said tubular shaft further comprising a biaxial lumen segment along less than an entire tubular shaft length and a coaxial lumen segment along less than said entire tubular shaft length, said biaxial lumen segment being located proximal to said coaxial lumen segment, said tubular shaft further comprising at least three lumens including at least a first lumen for passage of a stiffening wire or injection of fluids therethrough, said first lumen extending from said proximal hub partly through a length of said tubular shaft and terminating proximal to said coaxial lumen segment of said tubular shaft, at least a second lumen for injection of fluids or gases to inflate and deflate said expansile member, and at least a third lumen for passage of a guidewire therethrough extending from said distal tip end proximally through a guide wire port in a side wall of said tubular shaft, said first lumen further comprising an injection exit port disposed proximal to said coaxial lumen segment.

9. The angioplasty balloon catheter of claim 8 wherein said first lumen and said third lumen overlap along at least 1 mm of said length of said tubular shaft.

10. A method of performing an angioplasty of a blood vessel of a human patient, the method comprising:

a) Gaining percutaneous access to a vascular system in a human patient;

b) Advancing a guidewire and an angioplasty balloon catheter comprising a tubular shaft disposed between a proximal hub end and a distal tip end, said angioplasty balloon catheter further comprising an expansile member mounted to said tubular shaft disposed toward said distal tip end, said tubular shaft further comprising at least two lumens including at least a first lumen for passage of said guidewire and injection of fluids therethrough and at least a second lumen for injection of fluids or gases to inflate and deflate said expansile member, said tubular shaft further comprising a biaxial lumen segment of said first and second lumens along less than an entire tubular shaft length and a coaxial lumen segment of said first and second lumens along less than said entire tubular shaft length, said biaxial lumen segment being disposed proximal to said coaxial lumen segment, said tubular shaft further comprising at least one opening through a side wall along a length of said tubular shaft for egress of fluids injected into said first lumen, said at least one opening disposed proximal to said coaxial lumen segment, such that said angioplasty balloon catheter is in a location such that said expansile balloon is generally situated centrally on a blockage in a blood vessel;

c) Injecting radiopaque contrast fluid into said first lumen such that said radiopaque contrast fluid exits said at least one opening in said first lumen along said tubular shaft proximal to said expansile member and obtaining angiographic x-ray images;

d) Injecting fluids or gases into said second lumen to inflate said expansile balloon; and e) Aspirating said fluids or gases to deflate said expansile balloon.

11. A method of performing an angioplasty of a blood vessel of a human patient, the method comprising:

a) Gaining percutaneous access to a vascular system in a human patient;

b) Manipulating a guidewire and an angioplasty balloon catheter comprising a tubular shaft disposed between a proximal hub end and a distal tip end, said angioplasty balloon catheter further comprising an expansile member mounted to said tubular shaft disposed toward said distal tip end, said tubular shaft further comprising a biaxial lumen segment along less than an entire tubular shaft length and a coaxial lumen segment along less than said entire tubular shaft length, said biaxial lumen segment being disposed proximal to said coaxial lumen segment, said tubular shaft further comprising at least three lumens including at least a first lumen for passage of a stiffening wire or injection of fluids therethrough, said first lumen extending from said proximal hub partly through a length of said tubular shaft and terminating within said length of said tubular shaft, said tubular shaft further comprising at least one opening through a side wall along said length of said tubular shaft for egress of fluids injected into said first lumen, said at least one opening disposed proximal to said coaxial lumen segment, at least a second lumen for injection of fluids or gases to inflate and deflate said expansile member, and at least a third lumen for passage of said guidewire therethrough extending from said distal tip end proximally through a guide wire port in a side wall of said tubular shaft; so that said angioplasty balloon catheter is positioned in a location such that said expansile member is situated in a blockage in a blood vessel;

c) Injecting radiopaque contrast fluid into said first lumen such that said radiopaque contrast fluid exits a side hole in said first lumen along said tubular shaft proximal to said expansile member and obtaining angiographic x-ray images;

d) Injecting fluids or gases into said second lumen to inflate said expansile member; and e) Aspirating said fluids or gases to deflate said expansile balloon.

12. The method of performing an angioplasty of a blood vessel of a human patient of claim 11 wherein said angioplasty balloon catheter first lumen and said third lumen overlap along at least 1 mm of said length of said tubular shaft.

* * * * *